(12) United States Patent
Parissaux et al.

(10) Patent No.: US 11,098,135 B2
(45) Date of Patent: Aug. 24, 2021

(54) METHYLATED CYCLODEXTRINS AND METHODS FOR THE PRODUCTION THEREOF

(71) Applicant: Roquette Freres, Lestrem (FR)

(72) Inventors: Xavier Parissaux, Campagnes Lez Wardrecques (FR); Jean-Baptiste Palmieri, Lomme (FR); Mathias Ibert, La Chapelle d'Armentieres (FR); Clothilde Buffe, Lomme (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 15/767,958

(22) PCT Filed: Oct. 14, 2016

(86) PCT No.: PCT/FR2016/052658
§ 371 (c)(1),
(2) Date: Apr. 12, 2018

(87) PCT Pub. No.: WO2017/064436
PCT Pub. Date: Apr. 20, 2017

(65) Prior Publication Data
US 2018/0319903 A1 Nov. 8, 2018

(30) Foreign Application Priority Data

Oct. 16, 2015 (FR) ...................... 1559832

(51) Int. Cl.
| | | |
|---|---|---|
| *C08B 37/16* | (2006.01) | |
| *A61K 47/40* | (2006.01) | |
| *A61K 47/69* | (2017.01) | |
| *A61K 31/4965* | (2006.01) | |
| *A61K 31/724* | (2006.01) | |
| *C08L 5/16* | (2006.01) | |

(52) U.S. Cl.
CPC ...... *C08B 37/0012* (2013.01); *A61K 31/4965* (2013.01); *A61K 31/724* (2013.01); *A61K 47/40* (2013.01); *A61K 47/6951* (2017.08); *C08B 37/0015* (2013.01); *C08L 5/16* (2013.01); *C08L 2201/06* (2013.01); *C08L 2203/02* (2013.01)

(58) Field of Classification Search
None
See application file for complete search history.

(56) References Cited

U.S. PATENT DOCUMENTS

| | | |
|---|---|---|
| 5,710,268 A | 1/1998 | Wimmer |
| 5,935,941 A | 8/1999 | Pitha |
| 6,602,860 B1 | 8/2003 | Pitha |
| 7,259,153 B2 | 8/2007 | Chang |

FOREIGN PATENT DOCUMENTS

| | | | |
|---|---|---|---|
| CN | 1282662 C | 11/2006 | |
| EP | 0 193 850 A2 | 9/1986 | |
| JP | 62-220501 A | 9/1987 | |
| WO | WO 94/02516 A1 | 2/1994 | |
| WO | WO 94/22461 A1 | 10/1994 | |
| WO | WO-2013130666 A1 * | 9/2013 | ............ A61K 47/40 |
| WO | WO 2015/087016 A1 | 6/2015 | |

OTHER PUBLICATIONS

Theory and Application of Conductivity, Application Data Sheet, Rosemount Analytical Inc. Jan. 2010. (Year: 2010).*
M. Pumera et al., "Determination of Cyclodextrins and Their Derivatives by Capillary Electrophoresis with Indirect UV and Conductivity Detection." Fresenius J. Anal. Chem., vol. 369, pp. 666-669, 2001.
Qian Tingbao, "Application technology of Ion Exchanger," Tianjin Technical Science Press, the first edition pp. 115-118, Dec. 31, 1984.
Zhao Yingzheng, "Pharmaceutics of Biological Drugs," Hangzhou University Press, Jun. 2011, the first edition, pp. 85-87, Jun. 30, 2011.
The English translation of the Chinese Office Action, dated Dec. 19, 2019, in the related Chinese patent application No. 201680058923.X.

* cited by examiner

*Primary Examiner* — Layla D Berry

(57) ABSTRACT

The invention relates to a novel methylated cyclodextrin and to a novel method used for the production thereof. The invention also relates to the use of said methylated cyclodextrin for the solubilisation of lipophilic compounds, or carriers of at least one lipophilic group. The invention further relates to a composition comprising said methylated cyclodextrin, particularly a pharmaceutical composition.

10 Claims, 1 Drawing Sheet

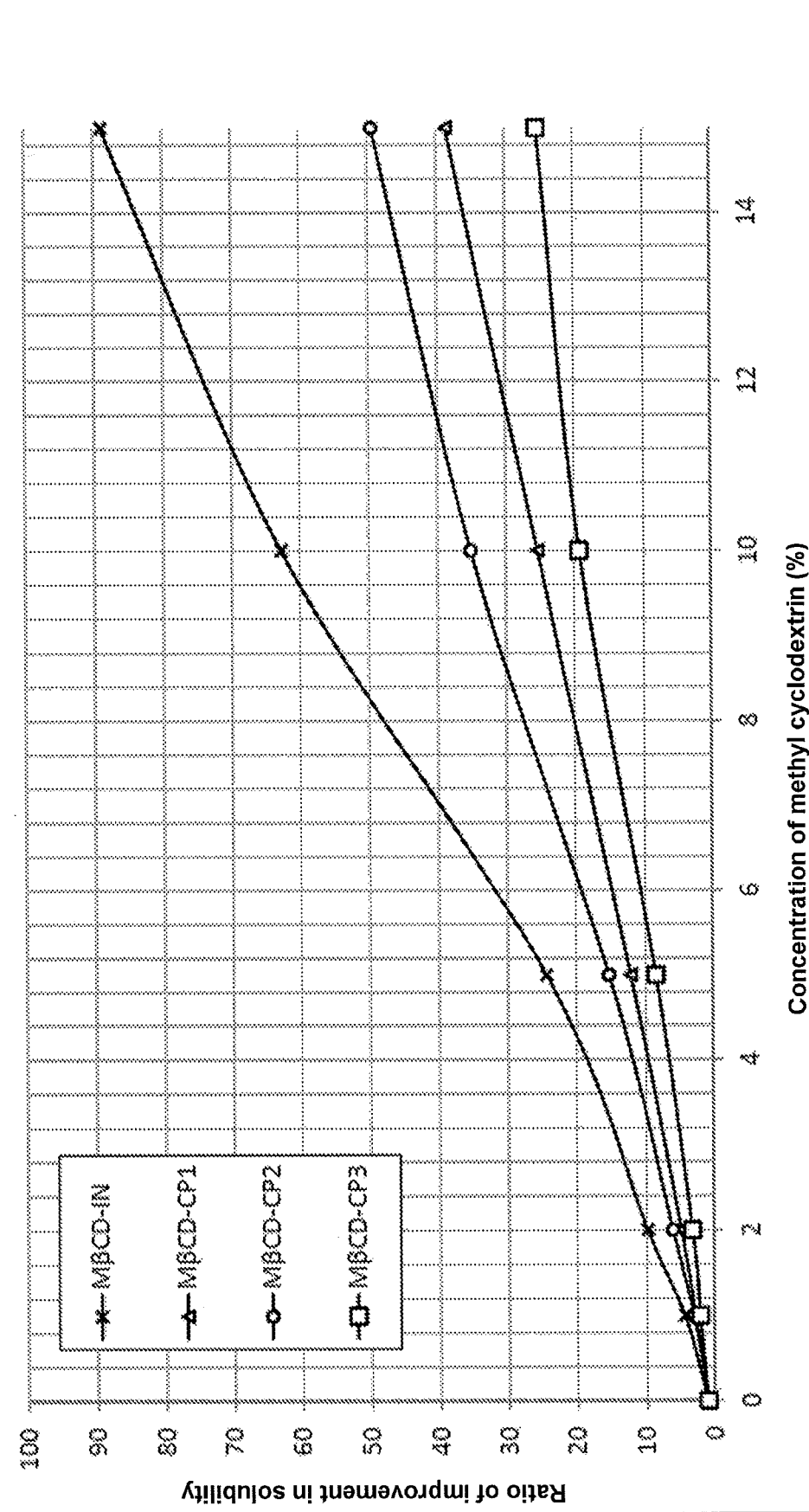

METHYLATED CYCLODEXTRINS AND METHODS FOR THE PRODUCTION THEREOF

CROSS REFERENCE TO RELATED APPLICATIONS

This application is a U.S. national stage application of International patent application No. PCT/FR2016/052658, filed Mar. Oct. 14, 2016, which claim the priority of French application No. 15 59832, filed Oct. 16, 2015, the subject matters of which are incorporated in their entirety by reference. herein.

The present invention relates to a novel methylated cyclodextrin, and also to a novel process of use for the preparation thereof. The invention also relates to the use of this methylated cyclodextrin, for the solubilization of lipophilic compounds or compounds bearing at least one lipophilic group. The invention also relates to a composition comprising this methylated cyclodextrin, especially a pharmaceutical composition, in particular intended to be used as medicament, and more particularly for use thereof in the treatment and/or the prevention of type 2 diabetes and/or complications thereof, and/or diseases able to be treated and/or prevented by an increase in the HDL cholesterol level and/or by a reduction in or prevention of atheromatous plaques, and/or diseases of the central nervous system.

CONTEXT OF THE INVENTION

Cyclodextrins are cyclic oligosaccharides resulting from the enzymatic degradation of starch. The three most common natural cyclodextrins are made up of 6, 7 or 8 α-D-glucopyranose units in chair configuration, linked to one another by α-1,4 bonds. They are more commonly referred to as α, β, or γcyclodextrin, respectively. Their three-dimensional structure appears in the form of a truncated cone, on the outside of which are the hydroxyl groups representing the highly hydrophilic part of cyclodextrins. The interior of the cone or the cavity of cyclodextrins is made up of the hydrogen atoms borne by the $C_3$ and $C_5$ carbons and also of the oxygen atoms which participate in the glycosidic bond, thus conferring on them a nonpolar nature.

Cyclodextrins having a hydrophilic external part and a hydrophobic cavity are generally used for their ability to encapsulate lipophilic compounds or groups and, therefore, for their role of protector and of solubilizer of these lipophilic compounds or compounds bearing lipophilic groups. They are thus conventionally found in the fields of food-processing, but also in galenics, where they are used as an excipient in pharmaceutical formulations.

The glucopyranose units of cyclodextrins each comprise 3 reactive hydroxyl groups, which are borne by the C2, C3 and C6 carbons. Numerous derivatives have thus already been synthesized by grafting different groups onto these hydroxyl functions, among which mention may be made of hydroxypropyl cyclodextrins, methyl cyclodextrins and sulfated derivatives.

Very recently, in its patent application WO 2015/087016 A1, the Applicant demonstrated in an original manner that some methyl cyclodextrins, characterized by a low degree of molar substitution (MS) of between 0.05 and 1.50, could be used not as excipient but as pharmaceutical active principle.

The Applicant showed in particular that these methyl cyclodextrins with a low MS were capable of acting effectively and specifically on lipid metabolism by increasing the plasma HDL cholesterol ("good cholesterol") level and by reducing triglyceridemia.

In this patent application, the Applicant envisaged the possibility of a galenical form which makes it possible to take advantage both of the pharmacological properties of these methyl cyclodextrins but also of their encapsulation properties. It was in particular a case of envisaging a complex in which this methyl cyclodextrin would have encapsulated a hydrophobic active principle having an additional pharmacological activity.

Unfortunately, the product used in this patent application has a relatively limited ability to solubilize lipophilic compounds.

The main aim of the present invention was therefore to improve this ability for solubilization of methyl cyclodextrin, in order to obtain an active agent/excipient with a greater efficacy.

The major constraint which the Applicant had to confront was that, in accordance with the teaching of the abovementioned patent application WO 2015/087016 A1, these methyl cyclodextrins absolutely had to have a low MS in order to be able to act effectively on lipid metabolism. Yet, it is known that weakly methylated cyclodextrins have a poorer ability to solubilize lipophilic compounds compared to highly methylated cyclodextrins (in this regard, see, for example: Kiss, T., Fenyvesi, F. et al.: Eur. J. Pharm. Sci. 40 (2010) 376-380).

Thus, in order to obtain a methyl cyclodextrin which is both pharmaceutically active and at the same time able to more effectively encapsulate lipophilic compounds, it was necessary to be able to reconcile properties which are a priori contradictory.

PRESENTATION OF THE INVENTION

The Applicant has achieved this after numerous studies which have culminated in the development of a methylated cyclodextrin with a low MS of between 0.05 and 1.50 which, unlike the product used in this previous patent application, has a low conductivity when it is in the form of an aqueous solution, of less than or equal to 50 µS/cm.

The methyl cyclodextrin of the invention was able to be obtained according to a novel process involving a step of decreasing the ionic species such that the conductivity of the methyl cyclodextrin is greatly reduced.

The use of methyl cyclodextrins as solubilizer for lipophilic active principles had of course already been envisaged in the prior art. However, these methyl cyclodextrins did not have the characteristics, and hence the efficacy of those of the invention.

U.S. Pat. No. 7,259,153 B2 for example describes the solubilization of lipophilic active principles by means of methyl cyclodextrins, in particular of methyl-β-cyclodextrins (MβCDs). However, these MβCDs did not have the combination of characteristics of the methyl cyclodextrins of the invention, and are much less effective for the solubilization of lipophilic compounds (see in particular the results obtained with the comparative methyl cyclodextrin "MβCD-CP1" in the example below).

It should be noted that, in this patent, the problem of solubilization was in principle solved by means of the use of crystallized MβCDs. The fact that these cyclodextrins need to be in crystalline form considerably limits the texturizing freedom of the product.

Other documents more generally describe processes for preparing methylated cyclodextrins. Among the rare documents actually describing the preparation of methyl cyclodextrins with a low MS, the Applicant still observed that the processes used did not make it possible to effectively separate the ionic species and hence to succeed in obtaining a product with low conductivity in accordance with the invention.

For example, the U.S. Pat. No. 6,602,860 B1 held by the Applicant, describes compositions comprising methyl cyclodextrins having an MS of less than 2. However, the process used did not make it possible to prepare a product with low conductivity in accordance with the invention. These MβCDs are much less effective than the methyl cyclodextrins of the invention for solubilizing lipophilic compounds (see in particular the results obtained with the comparative methyl cyclodextrin "MβCD-CP2" in the example below).

Moreover, these methyl cyclodextrins were characterized in that they were simultaneously in crystalline form and in amorphous form, yet it is industrially difficult to provide a product which always has the same crystalline/amorphous ratio. Moreover, in the presence of low moisture levels, the crystalline portion leads to the crystallization of the initially amorphous portion. This crystallization leads to a powder which has caking problems. In addition to the problem of reproducibility of the process, a relatively unstable product is therefore obtained.

Thus, the aim of the present invention is to provide a methylated cyclodextrin with a low MS which is more effective that the methylated cyclodextrins with low MS of the prior art, for the solubilization of lipophilic compounds or compounds bearing at least one lipophilic group.

More generally, an aim of the present invention is to provide a means for solubilization in aqueous medium of lipophilic compounds or compounds bearing at least one lipophilic group.

An aim of the present invention is in particular to provide a means for solubilization in aqueous medium of lipophilic compounds or compounds bearing at least one lipophilic group which also makes it possible to act positively on lipid metabolism, especially by increasing the serum HDL cholesterol level and/or by decreasing triglyceridemia.

Another aim of the present invention is to provide a cyclodextrin of use for improving the chemical stability of lipophilic compounds or compounds bearing at least one lipophilic group, and/or for improving the delivery thereof at and through biological membranes, and/or for increasing the physical stability thereof, and/or for converting them from a liquid form to a pulverulent form, and/or for preventing interactions with other compounds, and/or for reducing local irritation after a topical or oral administration of these lipophilic compounds or compounds bearing lipophilic groups, and/or for preventing the absorption thereof at certain tissues such as the skin, and/or for obtaining prolonged release of these compounds, and/or for masking the taste thereof, in particular the bitterness thereof, and/or for modifying the bioavailability thereof.

SUMMARY OF THE INVENTION

Thus, a first aim of the invention is a methyl cyclodextrin having a degree of molar substitution (MS) of between 0.05 and 1.50, characterized in that it has a conductivity of less than or equal to 50 μS/cm when it is in the form of a solution of distilled water at a concentration of 10%. Preferably, at least 50% of the methyl groups of said methyl cyclodextrin are located at the hydroxyl borne by the C2 carbon of the glucopyranose unit.

Preferably, the methyl cyclodextrin is a methyl-β-cyclodextrin.

Preferably, the methyl cyclodextrin is in pulverulent form. Optionally, it is in amorphous form.

In a preferred embodiment, it is in the form of a spray-dried product.

The present invention also relates to a process for preparing a methyl cyclodextrin having an MS of between 0.05 and 1.50, particularly useful for preparing methyl cyclodextrins according to the invention, comprising the step of decreasing the ionic species of the methyl cyclodextrin, such that the conductivity of said methyl cyclodextrin, when it is in the form of a solution of distilled water at a concentration of 10%, is reduced to a value of less than or equal to 50 μS/cm.

Preferably, this process comprises the steps:
(a) of etherification of a cyclodextrin with a methylation reagent, said etherification being carried out in basic medium, preferentially aqueous medium, at a temperature of between 100 and 200° C. and at a pressure between 1 and 10 bar;
(b) of decreasing the ionic species of the methyl cyclodextrin obtained in step (a), such that the conductivity of said methyl cyclodextrin, when it is in the form of a solution of distilled water at a concentration of 10%, is reduced to a value of less than or equal to 50 μS/cm;
(c) of drying the methyl cyclodextrin obtained in step (b);
(d) of recovering the methyl cyclodextrin obtained in step (c).

The step of decreasing the ionic species is preferably carried out by subjecting the methyl cyclodextrin in solution, in particular in aqueous solution, to:
an operation (b.1) of nanofiltration of the methyl cyclodextrin solution, said solution having a solids content by weight of less than or equal to 20%;
an operation (b.2) of demineralization on an ion-exchange column;
an operation (b.3) of decoloring with active carbon.

The present invention also relates to a composition comprising a methyl cyclodextrin according to the invention or comprising a methyl cyclodextrin obtained according to the process for preparing a methyl cyclodextrin of the invention. The composition also preferably comprises a lipophilic compound or a compound bearing at least one lipophilic group.

The present invention also relates to a composition of the invention for use thereof as medicament, preferably for use thereof in the treatment and/or the prevention of type 2 diabetes and/or complications thereof, and/or diseases able to be treated and/or prevented by an increase in the HDL cholesterol level and/or by a reduction in or prevention of atheromatous plaques, and/or diseases of the central nervous system.

The present invention also relates to the use of a methyl cyclodextrin according to the invention, or of a methyl cyclodextrin obtained according to the process for preparing a methyl cyclodextrin of the invention, for the solubilization of lipophilic compounds or compounds bearing at least one lipophilic group, and/or for improving the chemical stability thereof, and/or for improving the delivery thereof at and through biological membranes, and/or for increasing the physical stability thereof, and/or for converting them from a liquid form to a pulverulent form, and/or for preventing interactions with other compounds, and/or for reducing local irritation after a topical or oral administration of these lipophilic compounds or compounds bearing lipophilic groups, and/or for preventing the absorption thereof at certain tissues such as the skin, and/or for obtaining prolonged release of these compounds, and/or for masking the taste thereof, in particular the bitterness thereof, and/or for modifying the bioavailability thereof.

DETAILED DESCRIPTION OF THE INVENTION

The methyl cyclodextrins of the invention have a good capacity for solubilization of lipophilic agents or agents bearing lipophilic groups, while retaining a low MS, which is proof of its pharmacological activity on lipid metabolism.

This capacity for solubilization is greater than that of the MβOD used in patent application WO 2015/087016 A1. It is also greater than that of the MβCDs which are the subjects of U.S. Pat. Nos. 7,259,153 B2, 6,602,860 B1 and 5,935,941 A (see the example below).

The methyl cyclodextrins of the invention may thus advantageously be used for the solubilization of lipophilic active principles, or active principles bearing lipophilic groups, in pharmaceutical compositions. In these compositions, the methyl cyclodextrin of the invention may advantageously fulfil the role of encapsulation agent with regard to this other compound, and also the role of active principle.

Thus, the present invention relates to a pharmaceutical composition comprising a methyl cyclodextrin according to the present invention as active principle and/or as excipient. This pharmaceutical composition may also comprise another active principle, preferably a lipophilic active principle or an active principle bearing lipophilic groups, especially hypoglycemic agents.

Among these lipophilic active principles, mention may be made of the hypoglycemic agents used in type 2 diabetes, which are mostly very sparingly water soluble.

The use of the pharmacological properties of the methyl cyclodextrin would also be highly advantageous within the context of the treatment of this disease, since the majority of patients suffering from type 2 diabetes have, in addition to a characteristic hyperglycemia, mixed dyslipidemias. These mixed dyslipidemias are characterized by a reduction in the HDL cholesterol level and an increase in triglyceridemia, which are in fact regulated by methyl cyclodextrins with a low MS.

Another advantage of the methyl cyclodextrin of the invention is that the amorphous or crystalline form of the methyl cyclodextrin of the invention has no impact on its efficacy, which leaves a great degree of freedom in the texturization of the product and expands the field of possible galenical forms. It may for example be entirely in amorphous form, for example in the form of a spray-dried product.

The methyl cyclodextrin of the invention is primarily characterized by its degree of molar substitution (MS), which is between 0.05 and 1.50.

It is recalled here that the "degree of molar substitution (MS)" corresponds to the number of hydroxyl groups substituted by a methyl group per glucopyranose unit. It should be noted that the degree of molar substitution (MS) is different from the degree of molecular substitution (DS), which corresponds to the number of hydroxyl groups substituted by a methyl group per cyclodextrin molecule and which therefore takes into account the number of glucopyranose units constituting the methyl cyclodextrin.

The MS may conventionally be determined by those skilled in the art by proton nuclear magnetic resonance (NMR), or by mass spectrometry (electrospray ionization mass spectrometry (ESI-MS) or matrix-assisted laser desorption/ionization mass spectrometry (MALDI-MS)). While these techniques are well known to those skilled in the art, those skilled in the art may for example refer to the methods described in the reference thesis by Roman Jacquet: "Cyclodextrines hydrophiles: caractérisation et étude de leurs propriétés énantiosélective et complexante. Utilisation de la chromatographie en phase liquide et de la spectrométrie de masse" ["Hydrophilic cyclodextrins: characterization and study of their enantioselective and complexing properties. Use of liquid chromatography and mass spectrometry"]. Thesis on the chemistry and physicochemistry of compounds of biological interest. University of Orléans, 2006. Especially available at: http://tel.archives-ouvertes.fr/docs/00/18/55/42/PDF/jacquet.pdf (consulted on Nov. 27, 2013), in particular Chapter 2, Part B (pages 59 to 83).

Preferably, the MS is determined by NMR. It is possible in particular to proceed according to the method described below in the example under point B.1.

Preferentially, the MS of the methyl cyclodextrin according to the invention is between 0.10 and 1.40, preferentially between 0.10 and 1.30, preferentially between 0.20 and 1.20, preferentially between 0.30 and 1.10, preferentially between 0.30 and 1.00, preferentially between 0.50 and 0.90, preferentially between 0.60 and 0.80, for example between 0.60 and 0.70.

It should be noted that, although the methyl cyclodextrin of the invention may correspond to a pure product, it generally corresponds to a mixture of molecules of methyl cyclodextrin of different structures. It results therefrom that the MS measured is, in this case, an average of the substitutions which take place on all of the glucopyranose units of the entire mixture of molecules of methyl cyclodextrin.

This mixture may especially contain residual native cyclodextrin molecules, that is to say which are non-methylated, but which are generally and advantageously found in negligible amounts within the methyl cyclodextrin of the invention. Preferentially, the native cyclodextrins represent less than 1.0% of the methyl cyclodextrin, preferentially less than 0.5%, more preferentially still less than 0.1%, these percentages being expressed by dry weight.

The methyl cyclodextrin according to the invention is also characterized by its conductivity, which is less than or equal to 50 µS/cm.

This conductivity is in particular measured on the basis of a solution of distilled water in which the methyl cyclodextrin is at a concentration of 10%. It is in particular measured at a temperature of 25° C. It may readily be determined by those skilled in the art, for example according to the method recommended by the European Pharmacopeia with the reference "2.2.38. Conductivity, January 2008: 20238", used in the examples below.

Preferentially, the conductivity of the methyl cyclodextrin according to the invention is between 0 and 45 µS/cm, preferentially between 0 and 40 µS/cm, preferentially between 0 and 35 µS/cm, preferentially between 0 and 30 µS/cm, preferentially between 0 and 25 µS/cm, preferentially between 0 and 20 µS/cm. This conductivity is generally at least 1 µS/cm. It is for example chosen in the range extending from 1 to 15 µS/cm, or even from 1 to 10 µS/cm, or even from 5 to 10 µS/cm, or even from 6 to 10 µS/cm, or even from 7 to 10 µS/cm, or even from 8 to 10 µS/cm.

The methyl cyclodextrin according to the invention may be substituted on the hydroxyl borne by the C2 carbon of the glucopyranose units, or by the C3 and/or C6 carbons of the glucopyranose units or by a combination of the C2, C3 and/or C6, preferably C2 and C6, carbons of the glucopyranose units.

This distribution of the methyl groups on the hydroxyls of the glucopyranose unit of the methyl cyclodextrin may be conventionally determined by those skilled in the art by NMR.

Preferentially, at least 50% of the methyl groups of the methyl cyclodextrin of the invention are located at the hydroxyl borne by the C2 carbon of the glucopyranose unit, for example 50 to 80%, preferentially 60 to 80%, preferentially 65 to 80%, preferentially 70 to 80%, for example 75%.

In parallel, the other methyl groups are generally predominantly located at the hydroxyl borne by the C3 and/or C6 carbon of the glucopyranose unit.

Advantageously, the methyl cyclodextrin of the invention comprises 7 α-D-glucopyranose units. It is therefore a methyl-β-cyclodextrin.

In this case, the methyl-β-cyclodextrin preferentially has the following substitution profile:
- 0% to 5% of methyl-β-cyclodextrins comprise 2 methyl groups (DS of 2);
- 5% to 15% of methyl-β-cyclodextrins comprise 3 methyl groups (DS of 3);
- 20% to 25% of methyl-β-cyclodextrins comprise 4 methyl groups (DS of 4);
- 25% to 40% of methyl-β-cyclodextrins comprise 5 methyl groups (DS of 5);
- 15% to 25% of methyl-β-cyclodextrins comprise 6 methyl groups (DS of 6);
- 5% to 15% of methyl-3-cyclodextrins comprise 7 methyl groups (DS of 7);
- 0% to 5% of methyl-β-cyclodextrins comprise 8 methyl groups (DS of 8);

these percentages being molar percentages, and the total sum thereof being generally about 100%, although the composition may optionally contain traces of methyl cyclodextrins of different DS, and also traces of native cyclodextrin, i.e. non-methylated cyclodextrin.

The substitution profile may be conventionally determined by those skilled in the art, for example by ESI-MS or MALDI-TOF-MS. Although these techniques are well known to those skilled in the art, those skilled in the art may for example refer to the methods described in the above-mentioned thesis by Romain Jacquet in chapter 2, part B, points II.3 and II.2 (page 67 to 82) and in appendix II.

Generally and advantageously, the methyl cyclodextrin according to the invention has a reducing sugar content of less than 1.0% by dry weight, preferentially less than 0.5%.

Generally and advantageously, the methyl cyclodextrin of the invention comprises less than 100 ppm by dry weight of phosphates, preferentially less than 50 ppm, preferentially less than 10 ppm, more preferentially still less than 5 ppm.

Generally and advantageously, the methyl cyclodextrin of the invention comprises less than 20 ppm by dry weight of methylating agent, especially of dimethyl sulfate, preferentially less than 10 ppm, preferentially less than 5 ppm, more preferentially still less than 2 ppm.

Generally and advantageously, the methyl cyclodextrin of the invention comprises less than 1.0% of alkali metal halide salts, preferentially less than 0.5%, preferentially less than 0.2%, more preferentially still less than 0.1%; this percentage being expressed by dry weight of alkali metal halide salts relative to the total dry weight of said methyl cyclodextrin.

Preferably, the methyl cyclodextrin of the invention comprises:
- less than 100 ppm by dry weight of phosphates, preferentially less than 50 ppm, preferentially less than 10 ppm, more preferentially still less than 5 ppm;
- less than 20 ppm by dry weight of methylating agent, especially of dimethyl sulfate, preferentially less than 10 ppm, preferentially less than 5 ppm, more preferentially still less than 2 ppm; and
- less than 1.0% of alkali metal halide salts, preferentially less than 0.5%, preferentially less than 0.2%, more preferentially still less than 0.1%; this percentage being expressed by dry weight of alkali metal halide salts relative to the total dry weight of said methyl cyclodextrin.

Generally and advantageously, the methyl cyclodextrin of the invention has an absorbance at a wavelength of 245 nm to 270 nm of less than 0.5 AU, preferentially less than 0.3 AU, more preferentially still less than 0.2 AU; said absorbance being determined by UV/vis spectrophotometry, for an aqueous solution comprising 100 mg of said methyl cyclodextrin per ml of solution, in a cell having a path length of 1 cm.

This low absorbance advantageously reflects minimal reactivity of the methyl cyclodextrin with regard to other compounds.

Indeed, the degradation agents of the pharmaceutical active principles have the particular feature of having a maximum absorption at a wavelength of 245 nm to 270 nm. It is therefore these degradation agents which are measured by spectrophotometry at these wavelengths. "Degradation agents of the pharmaceutical active principles" is intended in particular to mean compounds, fragments or similar which degrade a pharmaceutical active principle in an aqueous solution. These degradation agents typically comprise compounds of molecular weight of less than 1000 Da, such as those generated by the preparation of methyl cyclodextrins, for example glycosidic fractions, decyclized cyclodextrin molecules, reducing sugars, glucose degradation products such as 3,4-dideoxyglucosone-3-ene, compounds bearing carbonyls such as 2-furaldehyde, or 5-hydroxymethyl-2-furaldehyde.

Generally and advantageously, the methyl cyclodextrin of the invention has an absorbance at a wavelength of 320 nm to 350 nm of less than 0.5 AU, preferentially less than 0.2 AU, more preferentially still less than 0.1 AU; said absorbance being determined by UV/vis spectrophotometry, for an aqueous solution comprising 100 mg of said methyl cyclodextrin per ml of solution, in a cell having a path length of 1 cm.

This absorbance, measured from 320 nm to 350 nm, makes it possible in particular to detect dyeing agents which are liable to interact with any active agents present.

The methyl cyclodextrin of the invention may also be grafted by chemical groups other than methyl groups, in a small proportion, and as long as this does not go against the properties desired in the present invention.

Preferentially, the methyl cyclodextrin of the invention does not comprise groups other than methyl groups. In particular, it is preferentially devoid of hydroxyalkyl groups, in particular of hydroxyethyl groups.

In a particular and advantageous embodiment, the methyl cyclodextrin of the invention is in pulverulent form. It may in this case be in amorphous form, in crystalline form, or in the form of a mixture of these two forms. It is preferentially either in amorphous form or in crystalline form, that is to say that it is preferentially not in the form of a mixture of these two forms. Most preferentially, the methyl cyclodextrin of the invention is in amorphous form.

Advantageously, the methyl cyclodextrin of the invention is in the form of a spray-dried product, that is to say in the form of a powder obtained by spray drying a solution of this methyl cyclodextrin, for example carried out in a single-stage spray-drying tower.

Advantageously, the pulverulent methyl cyclodextrin of the invention has a moisture level of less than 10%, for example less than 5%, for example of between 1 and 5%; this percentage corresponding to the weight of water relative to the total weight of said pulverulent methyl cyclodextrin.

The invention relates to a process for preparing a methyl cyclodextrin having an MS of between 0.05 and 1.50, particularly useful for preparing methyl cyclodextrins according to the invention, comprising the step of decreasing the ionic species of the methyl cyclodextrin, such that the conductivity of said methyl cyclodextrin, when it is in the form of a solution of distilled water at a concentration of 10%, is reduced to a value of less than or equal to 50 µS/cm.

More particularly, the invention also relates to a process for preparing a methyl cyclodextrin having an MS of between 0.05 and 1.50, particularly useful for preparing methyl cyclodextrins according to the invention, comprising the steps:
(a) of etherification of a cyclodextrin with a methylation reagent, said etherification being carried out in basic medium, preferentially aqueous medium, at a temperature of between 100 and 200° C. and at a pressure between 1 and 10 bar;
(b) of decreasing the ionic species of the methyl cyclodextrin obtained in step (a), such that the conductivity of said methyl cyclodextrin, when it is in the form of a solution of distilled water at a concentration of 10%, is reduced to a value of less than or equal to 50 µS/cm;
(c) of drying the methyl cyclodextrin obtained in step (b);
(d) of recovering the methyl cyclodextrin obtained in step (c).

Preferentially, the methylation reagent to which step (a) refers is dimethyl sulfate.

Preferentially, step (a) of etherification is carried out at a temperature of between 90 and 190° C., preferentially between 100 and 180° C., preferentially between 110 and 170° C., preferentially between 120 and 160° C., preferentially between 130 and 150° C., for example equal to 140° C.

Preferentially, step (a) of etherification is carried out at a pressure of between 2 and 9 bar, preferentially between 2 and 8 bar, preferentially between 2 and 7 bar, preferentially between 2 and 6 bar, preferentially between 3 and 5 bar, for example equal to 4 bar.

The reaction medium of step (a) may advantageously be rendered basic by addition of calcium hydroxide. The reaction may then for example be neutralized with sulfuric acid.

The step (b) may in particular be carried out by subjecting the methyl cyclodextrin in solution, in particular in aqueous solution, to:
an operation (b.1) of nanofiltration of the methyl cyclodextrin solution, said solution having a solids content by weight of less than or equal to 20%;
an operation (b.2) of demineralization on an ion-exchange column;
an operation (b.3) of decoloring with active carbon;
said steps (b.1), (b.2) and (b.3) being preferentially carried out in this order or in the following order: (b.1), (b.3) and (b.2).

Step (b) may be preceded by a step of filtration or spin-drying and of washing, in particular in order to eliminate the calcium sulfate liable to form (depending on the methylation reagent chosen and also on the acid used to neutralize the reaction).

Preferentially step (c) of drying is a step of spray drying.

This spray drying may be single-stage or multi-stage spray drying. In the case of multi-stage spray drying, the spray dryer is coupled to a fluidized bed, optionally integrated with the spray-drying tower, which makes it possible to agglomerate the particles formed by spray drying. The latter process is particularly beneficial if it is desired to obtain powders of greater mean diameter and depending on the flow desired for the resulting powder.

The invention also relates to a composition comprising a methyl cyclodextrin according to the invention or comprising a methyl cyclodextrin obtained according to the process for preparing a methyl cyclodextrin of the invention.

The composition according to the invention also preferentially comprises at least one lipophilic compound or compound bearing at least one lipophilic group.

This may for example be hydrophobic compounds, that is to say conventionally compounds which are sparingly water-soluble or highly sparingly water-soluble or even practically water-insoluble at room temperature (15-25° C.). "Sparingly water-soluble compound" is conventionally intended to mean that a volume of water from 100 to 1000 ml is required to dissolve 1 gram of said compound. For a "highly sparingly water-soluble compound", this volume of water is more than 1000 ml and ranges up to 10 000 ml. For a "practically water-insoluble compound", this volume of water is more than 10 000 ml. In this regard, see in particular the definition given in the European Pharmacopeia with the reference "1.4 Monographs, July 2014: 10 000".

Preferentially, the lipophilic compound or compound bearing at least one lipophilic group to which the invention refers is a pharmaceutical active principle, preferentially selected from hypoglycemic agents and mixtures thereof. Hypoglycemic agents essentially comprise metformin, sulfonylureas such as glibenclamide, gliclazide, glimepiride, glipizide, or gliquidone, glitazones, gliptines GLP-1 (Glucagon-Like Petide-1) agonists, such as exenatide and liraglutide, acarbose, nateglinide, and repaglinide. Preferentially, this hypoglycemic agent is selected from sulfonylureas and it is most preferentially glipizide. The pharmaceutical active principle in question may also be selected from statins, antihypertensive agents, angiotensin-II receptor agonists, also referred to as "sartans", beta blockers, platelet aggregation inhibitors or anticoagulants.

Preferentially, the compositions of the invention are pharmaceutical compositions or compositions for use thereof as medicament, for example for use in the treatment and/or prevention of type 2 diabetes and/or complications thereof. Since the compositions of the invention are also capable of acting on lipid metabolism, they may also be used in the treatment and/or prevention of diseases that are liable to be treated and/or prevented by an increase in the HDL cholesterol level and/or by a reduction or prevention of atheromatous plaques, in particular atherosclerosis or complications relating to an atheroma, and/or diseases of the central nervous system, in particular Alzheimer's disease, Parkinson's disease or Niemann Pick disease type C.

The diseases that are liable to be treated and/or prevented by an increase in the HDL cholesterol level are typically diseases associated with overload, and/or with storage and/or with accumulation of cholesterol in the tissues, and also the consequences thereof. This includes, for example, cardiovascular diseases, vascular diseases, occlusive peripheral arterial diseases such as atherosclerosis or complications relating to an atheroma, diseases of the central nervous system, such as Alzheimer's disease, Parkinson's disease and lysosomal diseases affecting the central nervous system such as, for example, Niemann Pick disease, such as Niemann Pick disease type A, Niemann Pick disease type B, or Niemann Pick disease type C. The complications relating to an atheroma which are treated and/or prevented by the use of a pharmaceutical composition according to the invention are, in a nonlimiting manner, ischemia, for example myocardial ischemia, coronary diseases, angina pectoris, acute coronary syndrome, myocardial infarction, mesenteric infarction, stroke, aneurysm or arteriopathy of the lower limbs.

The present invention also relates to the use of a pharmaceutical composition according to the present invention for the production of a medicament, especially intended for treating and/or preventing the abovementioned conditions and diseases. It also relates to a method for treating and/or preventing the abovementioned conditions and diseases in a subject, comprising the administration of a therapeutically effective amount of a pharmaceutical composition according to the present invention.

The compositions of the invention may be in any galenical form deemed to be suitable by those skilled in the art, depending on the targeted use. They may for example be in liquid, solid or semi-solid form. They may for example be solutions, suspensions, dispersions, emulsions, pellets, granules, films, powders, gels, creams, ointments, pastes, sticks, tablets, hard gel capsules, soft capsules, osmotic devices, patches.

The compositions of the invention may moreover comprise any other additional and usual compound, as long as this does not go against the properties desired in the present invention.

These compounds are typically chosen as a function of the galenical form selected for the composition.

The compositions of the invention are capable of being administered orally, parenterally, cutaneously or mucosally. The parenteral route comprises for example subcutaneous, intravenous, intramuscular or intraperitoneal administration, although the latter is rather reserved for animals. The mucosal route comprises for example nasal administration, pulmonary administration or administration via the rectal mucosa. The cutaneous route comprises for example the dermal route, especially via a transdermal device, typically a patch. For the treatment and/or prevention of diseases of the central nervous system, the intrathecal route or the spinal route are also able to be employed.

Finally, the invention relates to the use of a methyl cyclodextrin according to the invention or of a methyl cyclodextrin obtained according to the process for preparing a methyl cyclodextrin according to the invention, for the solubilization in aqueous medium of lipophilic compounds or compounds bearing at least one lipophilic group, said compound preferentially being as defined above.

The invention also relates to the use of a methyl cyclodextrin according to the invention, or of a methyl cyclodextrin obtained according to the process for preparing a methyl cyclodextrin of the invention, for improving the chemical stability of lipophilic compounds or compounds bearing at least one lipophilic group, and/or for improving the delivery thereof at and through biological membranes, and/or for increasing the physical stability thereof, and/or for converting them from a liquid form to a pulverulent form, and/or for preventing interactions with other compounds, and/or for reducing local irritation after a topical or oral administration of these lipophilic compounds or compounds bearing lipophilic groups, and/or for preventing the absorption thereof at certain tissues such as the skin, and/or for obtaining prolonged release of these compounds, and/or for masking the taste thereof, in particular the bitterness thereof, and/or for modifying the bioavailability thereof.

It should be noted that, in the present invention, it is understood that the expression "between X and Y" covers a range of values excluding the limit values mentioned.

It is moreover understood that when reference is made to the concentration in percentage of a substance in solution, this concentration expresses the number of grams of said substance per 100 ml of said solution. This weight in grams is indeed a dry weight, that is to say that it especially excludes the weight of water which may be present in the substance in its pulverulent form before solubilization.

The invention will be understood more clearly from the following examples which are intended to be illustrative and nonlimiting.

FIGURE

FIG. 1 describes the ratio of improvement in solubility as a function of the concentration of methyl cyclodextrin for several samples of methyl cyclodextrin ("MβCD-IN", "MβCD-CP1", "MβCD-CP2" and "MβCD-CP3").

EXAMPLE

In the following tests, a methyl-β-cyclodextrin according to the invention ("MβCD-IN") was compared to methyl-β-cyclodextrins using processes of the prior art ("MβCD-CP1", "MβCD-CP2" and "MβCD-CP3").

The inventors proceeded such that these MβCDs all have an MS of 0.7, so as to be able to effectively compare these MβCDs on the basis of the criterion of conductivity.

A. Methyl-β-Cyclodextrins (MβCDs) Used

1. Preparation of an MβCD According to the Invention (MβCD-IN)

A native β-cyclodextrin was etherified in dimethyl sulfate, in aqueous medium and in the presence of calcium hydroxide, under the following temperature and pressure conditions: 140° C./4 bar. The reaction medium was then neutralized with sulfuric acid.

The reaction product was then spin-dried (Dorr-Oliver BW630H spin dryer) and washed, in order to eliminate the calcium sulfate formed during the reaction. The washing was in particular carried out by spray nozzle with demineralized water heated to 70° C. 3.5 tons of reaction product with 23% dry matter content were thus obtained.

The ionic species of the reaction product obtained in this way were separated by the following operations:
  nanofiltration of the solution adjusted to 20% dry matter content;
  demineralization on ion-exchange column;
  decoloring with active carbon.

The nanofiltration step was in particular carried out under the following conditions: use of AFC30 membranes; use of two 1.7 m² tubes in parallel (3.4 m² in total); 2.7 m²/h high-pressure pump; counter-pressure set at 20 bar module inlet; solution of MβCD adjusted to 20% dry matter content, brought to a temperature of 55° C. and to a pH of 5.5; permeate flow rate of from 70 to 85 l/h/m²; outlet pressure of 18 bar. 6 filtrations were thus carried out.

The demineralization step was in particular carried out under the following conditions:
  treatment at a temperature of less than 40° C., 50 l/h, at 20% dry matter content:
    cationic (Amberlite 252); 25 liters; 1.8 eq/l;
    anionic (Amberlite IRA 910); 40 liters; 1.1 eq/l;
    mixed bed; 30 liters;
  2 700 l tanks were demineralized before regeneration.

The step of decoloring with active carbon (NORIT SX plus) was in particular carried out under the following conditions: solution of MβCD at 20% dry matter content, treated with 1% black; stirring for 1 hour; pH 5-5.5; room temperature; filtration on 11 μm sleeve, then 8 μm, and finally 0.22 μm.

The MβCD obtained in this way was then concentrated so as to have a dry matter content by weight of 30%, by means of an evaporator (NIRO), in particular under the following conditions: supply flow rate of 100 l/h; product temperature of 62° C.; pressure of 200 mbar.

The solution obtained in this way was dried by single-stage spray drying (NIRO spray dryer). The conditions were in particular the following: solution to be spray dried adjusted to a temperature of 70° C. and to a pH of 6.5-7; filtration of the solution (0.22 μm); temperature of the inlet air of 250° C.; temperature of the outlet air regulated to 115° C.; air flow rate of 120 Nm$^3$/h; negative pressure adjusted to 35 mm of water; flow rate of the spray-dried product of 6.8 to 7 kg/h.

The pulverulent MβCD obtained in this way (MβCD-IN) had a moisture content of 3.5%, a content of reducing sugars of 0.3% and a content of residual native β-cyclodextrin of less than 0.1%.

2. Comparative MβCDs (MβCD-CP1, -CP2 and -CP3)

The comparative methyl cyclodextrin "MβCD-CP1" corresponds to that used in U.S. Pat. No. 7,259,153 B2 and designated "Cryst. Methylated β-CD" in this patent. Although no process for preparing this MβCD is described in this patent, and this product is not commercially available, the inventors worked on the assumption that it was prepared according to U.S. Pat. No. 5,935,941 A. Indeed, this patent is cited as a promising basis for preparing the MβCD of U.S. Pat. No. 7,259,153 B2. The inventors based this in particular on example 15 of U.S. Pat. No. 5,935,941 A, the only example illustrating the preparation of methylated cyclodextrins. The reaction product was in particular treated according to the methods described in example 1 of this document.

The comparative methyl cyclodextrin "MβCD-CP2" was prepared according to U.S. Pat. No. 6,602,860 B1. The reaction product was in particular treated according to the methods described in example 1 of this document.

The comparative methyl cyclodextrin "MβCD-CP3" corresponds to the product sold under the name KLEPTOSE® Crysmeb, used in patent application WO 2015/087016 A1. This product is in particular obtained according to the U.S. Pat. No. 9,935,941 A, except for the fact that it is dried by spray drying.

B. Characterization

The characteristics of the methyl cyclodextrins MβCD-IN, MβCD-CP1, MβCD-CP2 and MβCD-CP3 were determined according to the following methods.

1. Determination of the Degree of Molar Substitution (MS) and the Substitution Profile The MS was determined by proton NMR (on a DPX 250 MHz Advance apparatus (Bruker, Rheinstetten, Germany)). The measurements were taken at 25° C. The calibration was carried out with the D$_2$O signal. The samples of MβCD, and of native cyclodextrin, i.e. non-methylated cyclodextrin, were prepared at a concentration of 5 mg in 0.75 ml of D$_2$O. The solutions were evaporated to dryness under a nitrogen stream and then reconstituted in 0.75 ml of D$_2$O. This operation was repeated twice in order to ensure total exchange of the protons of the hydroxyl functions. The MS was calculated from the difference in integration between the spectrum of the native cyclodextrin and that of the methyl cyclodextrin in accordance with the invention. The NMR spectrum also made it possible to calculate the substitution profile.

2. Determination of the Conductivity

The conductivity was determined at 25° C. according to the method recommended by the European Pharmacopoeia, reference "2.2.38. Conductivity, January 2008: 20238" on the basis of a 100 ml solution at 10% of MβCD. In particular, 10 dry grams of MβCD were placed in a 100 ml volumetric flask. Distilled water having a resistivity of greater than 500 000 ohms·cm was added (q.s. 100 ml).

The conductivity of this solution was in particular determined by means of an electronic conductivity meter (KNICK 703) fitted with a measurement cell and verified according to the procedure described in the related instructions.

The results obtained are given in Table 1.

TABLE 1

| | MβCD | | | |
|---|---|---|---|---|
| | MβCD-IN | MβCD-CP1 | MβCD-CP2 | MβCD-CP3 |
| Degree of molar substitution (MS) | 0.67 | 0.67 | 0.68 | 0.67 |
| Substitution profile | 75% of the substitutions borne by C2 carbons | ND | ND | ND |
| Conductivity | 9 μS/cm | 89 μS/cm | 62 μS/cm | 102 μS/cm |

ND: not determined

C. Test of Solubilization of Glipizide

The methyl cyclodextrin MβCD-IN according to the invention and the comparative methyl cyclodextrins MβCD-CP1, MβCD-CP2 and MβCD-CP3 were evaluated for their ability to solubilize glipizide in distilled water, according to the following method: 6 solutions at 0, 1, 2, 10 and 15% of MβCD were prepared, for each MβCD. Distilled water was used as control solution. These solutions were stirred at room temperature. Glipizide was added milligram by milligram until it no longer dissolved. The limit amount of glipizide dissolving was noted for each solution, which made it possible to calculate the number of mg of glipizide dissolved per ml of solution.

The ratio of improvement in solubility gives the factor by which the solubility is increased in the presence of a defined concentration of methyl cyclodextrin. It is calculated as follows:

$$\text{Solubility ratio} = \frac{S_{MCD}}{S_{H2O}}$$

with: "$S_{MCD}$" expressed in mg of glipizide solubilized per ml of solution of methyl cyclodextrin; "$S_{H2O}$" expressed in mg of glipizide solubilized per ml of water.

The results are shown in FIG. 1.

It is observed that the ratio of improvement in solubility is much higher as regards the methyl cyclodextrin MβCD-IN according to the invention compared to the methyl cyclodextrins MβCD-CP1, MβCD-CP2 and MβCD-3, not in accordance with the invention.

It may be deduced that at low MSs, a methyl cyclodextrin having a conductivity less than or equal to 50 μS/cm, such as the methyl cyclodextrin MβCD-IN according to the invention, is a much better solubilizer of lipophilic compounds or compounds bearing lipophilic groups.

The invention claimed is:

1. A process for preparing a methyl cyclodextrin having a MS of between 0.05 and 1.50, comprising the step of decreasing ionic species of the methyl cyclodextrin, such that the conductivity of said methyl cyclodextrin, when it is in the form of a solution of distilled water at a concentration of 10%, is reduced to a value of less than or equal to 50 μS/cm, wherein the step of decreasing the ionic species is carried out by subjecting the methyl cyclodextrin in solution to:
an operation (b.1) of nanofiltration of the methyl cyclodextrin solution, said solution having a solids content by weight of less than or equal to 20%;
an operation (b.2) of demineralization on an ion-exchange column; and
an operation (b.3) of decoloring with active carbon.

2. A process for preparing a methyl cyclodextrin having a degree of molar substitution (MS) of between 0.05 and 1.50, comprising the steps of:
(a) etherification of a cyclodextrin with a methylation reagent, said etherification being carried out in basic medium, at a temperature of between 100 and 200° C. and at a pressure between 1 and 10 bar;
(b) decreasing ionic species of the methyl cyclodextrin obtained in step (a), such that the conductivity of said methyl cyclodextrin, when it is in the form of a solution of distilled water at a concentration of 10%, is reduced to a value of less than or equal to 50 μS/cm;
(c) drying the methyl cyclodextrin obtained in step (b); and
(d) recovering the methyl cyclodextrin obtained in step (c);
wherein the step of decreasing the ionic species is carried out by subjecting the methyl cyclodextrin in solution to:
an operation (b.1) of nanofiltration of the methyl cyclodextrin solution, said solution having a solids content by weight of less than or equal to 20%;
an operation (b.2) of demineralization on an ion-exchange column; and
an operation (b.3) of decoloring with active carbon.

3. A composition comprising a methyl cyclodextrin having a degree of molar substitution (MS) of between 0.05 and 1.50 and a conductivity of less than or equal to 50 μS/cm when it is in the form of a solution of distilled water at a concentration of 10%, and also comprising a compound bearing at least one lipophilic group selected from hypoglycemic agents and mixtures thereof.

4. A medicament comprising the composition of claim 3.

5. A process of treatment and/or prevention of type 2 diabetes and/or complications thereof, and/or diseases able to be treated and/or prevented by an increase in the HDL cholesterol level and/or by a reduction in or prevention of atheromatous plaques, and/or diseases of the central nervous system comprising administering the composition of claim 3.

6. A method comprising administering a methyl cyclodextrin obtained according to the process of claim 1 to a subject, for at least one of the solubilization of one of lipophilic compounds or compounds bearing at least one lipophilic group, improving the chemical stability thereof, improving the delivery thereof at and through biological membranes, increasing the physical stability thereof, converting them from a liquid form to a pulverulent form, preventing interactions with other compounds, reducing local irritation after a topical or oral administration of these lipophilic compounds or compounds bearing lipophilic groups, preventing the absorption thereof at certain tissues obtaining prolonged release of these compounds, masking the taste thereof, and modifying the bioavailability thereof, wherein the lipophilic compound or compound bearing at least one lipophilic group is selected from hypoglycemic agents and mixtures thereof.

7. A composition comprising the methyl cyclodextrin prepared according to the process as defined in claim 1, and also comprising at least one lipophilic compound or compound bearing at least one lipophilic group selected from hypoglycemic agents and mixtures thereof.

8. A composition comprising the methyl cyclodextrin prepared according to the process as defined in claim 2, and also comprising at least one lipophilic compound or compound bearing at least one lipophilic group selected from hypoglycemic agents and mixtures thereof.

9. A method for the solubilization in aqueous medium of lipophilic compounds or compounds bearing at least one lipophilic group selected from hypoglycemic agents and mixtures thereof comprising combining with said the methyl cyclodextrin prepared according to the process as defined in claim 1 with said lipophilic compounds or compounds bearing at least one lipophilic group selected from hypoglycemic agents and mixtures thereof.

10. A method for the solubilization in aqueous medium of lipophilic compounds or compounds bearing at least one lipophilic group selected from hypoglycemic agents and mixtures thereof comprising combining with said the methyl cyclodextrin prepared according to the process as defined in claim 2 with said lipophilic compounds or compounds bearing at least one lipophilic group selected from hypoglycemic agents and mixtures thereof.

* * * * *